United States Patent [19]

Sawano et al.

[11] Patent Number: 6,093,868
[45] Date of Patent: Jul. 25, 2000

[54] EYE BANDAGE USED AFTER INTRAOCULAR SURGICAL OPERATION

[75] Inventors: Tadashi Sawano, Aichi-ken; Hiroyuki Ohyama; Yuuji Gotou, both of Kakamigahara, all of Japan

[73] Assignee: Menicon Co., Ltd., Japan

[21] Appl. No.: 09/189,825

[22] Filed: Nov. 10, 1998

[30] Foreign Application Priority Data

Nov. 20, 1997 [JP] Japan ................................ 9-320015

[51] Int. Cl.$^7$ ................................ A61F 5/00; G02C 7/04
[52] U.S. Cl. ................................ 602/43; 602/41; 602/42; 351/160 R
[58] Field of Search ................... 602/41–56; 351/160 R, 351/161, 162, 163, 160 H; 128/858, 888; 523/106; 525/937

[56] References Cited

U.S. PATENT DOCUMENTS 4,561,737 12/1985 Bourset et al. ................ 351/160 R

FOREIGN PATENT DOCUMENTS

| 0 407 646 A1 | 1/1991 | European Pat. Off. . |
| 55-101125 | 7/1980 | Japan . |
| 59-500799 | 5/1984 | Japan . |
| 655901 | 8/1951 | United Kingdom . |
| 952918 | 3/1964 | United Kingdom . |
| 83 03963 | 11/1983 | WIPO . |

OTHER PUBLICATIONS

Beltz, Linda, Hope For Nearsightedness, The World Wide Web, pp. 1–3, Feb. 1997.

*Primary Examiner*—Kim M. Lee
*Attorney, Agent, or Firm*—Wall Marjama Bilinski & Burr

[57] ABSTRACT

An eye bandage formed of a soft material and having a shape similar to a contact lens, the eye bandage being worn on an eye after an intraocular surgical operation of the eye, such that the eye bandage is held in contact with a cornea and a sclera of the eye so as to cover an incised portion of the sclera, the eye bandage comprising: a central portion which is to contact the cornea and which has a back surface having a profile following that of a front surface of the cornea; and a peripheral portion located radially outwardly of the central portion and having a thickness larger than that of the central portion and a diameter which is large enough to cover the incised portion of the sclera, the peripheral portion including at least a sclera-contacting portion that is to contact the sclera, the sclera-contacting portion having a back surface having a profile following a front surface of the sclera, so that the sclera-contacting portion is held in close contact with the sclera of the eye.

10 Claims, 2 Drawing Sheets

EYE BANDAGE USED AFTER INTRAOCULAR SURGICAL OPERATION

The present application is based on Japanese Patent Application No. 9-320015 filed Nov. 20, 1997, the content of which is incorporated hereinto by reference.

BACKGROUND OF THE INVENTION

1. Field of the Invention

The present invention relates to an eye bandage which is worn on an eyeball of an eye after an intraocular surgical operation, so as to cover an incised portion of the sclera.

2. Discussion of the Related Art

In order to protect the eye which has been subjected to an intraocular surgical operation in which the cornea or the sclera of the eye is incised, various measures are generally taken to treat the incised portion of the cornea or the sclera.

As well known, trabeculectomy is a surgical technique to treat glaucoma of an eye, in which the sclera is incised so as to resect the trabecula. At the incised portion of the sclera, there are formed filtration blebs through which the aqueous humor is drained or discharged to the subconjunctival space, to thereby prevent a rise of the intraocular pressure which would be caused by accumulation of an excessive amount of the aqueous humor between the cornea and the crystalline lens.

After the surgical operation described above, it is necessary to prevent an excessive amount of drainage of the aqueous humor from the filtration blebs, which may undesirably cause a considerable decrease in the intraocular pressure, resulting in various troubles with the eye. For preventing the excessive drainage of the aqueous humor, the filtration blebs are pressed by using suitable medical or therapeutic devices.

As one example of such medical devices to press the filtration blebs, a so-called "pressure patching" is conventionally used. Since the pressure patching is worn so as to cover the whole eye of the patient, the vision of the patient is lost.

In the light of the above drawback, it is proposed to use an eye bandage in place of the pressure patching. The eye bandage is worn directly on the eyeball such that it is held in contact with the cornea and the sclera, so as to cover the incised portion of the sclera. This eye bandage has a shape similar to that of a contact lens, and is formed of a transparent soft material, so that the vision of the patient's eye fitted with the bandage is not lost, while at the same time the patient enjoys a good wearing comfort of the eye bandage. Since the shape of the eye bandage is similar to that of the contact lens, the eye bandage can be easily worn on the eyeball of the patient just as the contact lens is worn on the eye.

The conventional eye bandage described above has a central portion which is to contact the cornea and corresponds to an optical portion of a soft contact lens generally used for rectifying the eyesight of the wearer. The conventional eye bandage, however, is not designed to press the filtration blebs of the incised portion of the sclera when it is worn on the eyeball, failing to press the filtration blebs as required. Thus, the conventionally used eye bandage is not satisfactory in preventing the excessive drainage of the aqueous humor from the filtration blebs.

SUMMARY OF THE INVENTION

The present invention was developed in the light of the above situations. It is therefore an object of the invention to provide an eye bandage which is worn on an eye after an intraocular surgical operation wherein the sclera of the eye is incised, which eye bandage is capable of sufficiently pressing the incised portion of the sclera while it is worn on the eyeball, so that the eye bandage effectively prevents excessive drainage of the aqueous humor from the filtration blebs formed in the incised portion after the surgical operation to treat glaucoma, for instance.

The above object of the present invention may be attained according to a principle of the present invention, which provides an eye bandage formed of a soft material and having a shape similar to a contact lens, the eye bandage being worn on an eye after an intraocular surgical operation of the eye, such that the eye bandage is held in contact with a cornea and a sclera of the eye so as to cover an incised portion of the sclera, the eye bandage comprising: a central portion which is to contact the cornea and which has a back surface having a profile following that of a front surface of the cornea; and a peripheral portion located radially outwardly of the central portion and having a thickness larger than that of the central portion and a diameter which is large enough to cover the incised portion of the sclera, the peripheral portion including at least a sclera-contacting portion that is to contact the sclera, the sclera-contacting portion having a back surface having a profile following a front surface of the sclera, so that the sclera-contacting portion is held in close contact with the sclera of the eye.

The eye bandage according to the present invention is worn on the eyeball such that the central portion is held in contact with the cornea and such that the peripheral portion is held in pressing contact with the sclera and the incised portion while covering the entirety of the incised portion. In the present eye bandage, the peripheral portion is thicker than the central portion, whereby the rigidity of the peripheral portion is effectively enhanced, so that the peripheral portion does not suffer from flexural or bending deformation while it is worn on the eyeball. Accordingly, this arrangement minimizes otherwise possible formation of a gap or spacing between the peripheral portion of the eye bandage and the sclera including the incised portion, whereby the peripheral portion of the present eye bandage is effectively held in close contact with the sclera and the incised portion. When the filtration blebs are formed in the incised portion due to accumulation of the aqueous humor, the filtration blebs in the incised portion can be held in pressing contact with the highly rigid peripheral portion of the eye bandage. In addition, the thick-walled, rigid peripheral portion of the present eye bandage can be pressed tightly against the sclera by the eye lid when the eye bandage is worn on the eyeball.

When the present eye bandage is worn on the eyeball, it is capable of pressing the incised portion formed in the sclera after the intraocular surgical operation to treat the glaucoma, for instance. Accordingly, the present eye bandage can effectively press the filtration blebs formed in the incised portion, to thereby prevent excessive drainage of the aqueous humor from the filtration blebs, allowing early recovery of the incised eye after the surgical operation.

In a first preferred form of the present invention, the outside diameter of the peripheral portion of the eye bandage is in the range of 16–22 mm. If the outside diameter of the peripheral portion is smaller than 16 mm, the surface area of the sclera-contacting portion of the peripheral portion is not large enough to cover the entirety of the incised portion formed in the sclera. On the other hand, if the outside diameter of the peripheral portion exceeds 22 mm, the size of the eye bandage is too large, making the insertion of the eye bandage difficult.

In a second preferred form of the present invention, the thickness of the central portion is in the range of 0.03–0.15 mm. The thickness of the central portion smaller than 0.03 mm makes the manufacture of the eye bandage difficult, and results in considerably reduced mechanical strength of the eye bandage. On the other hand, the thickness of the central portion exceeding 0.15 mm undesirably reduces an amount of oxygen which permeates through the central portion to the cornea. In this case, the cornea may be damaged due to anoxia during wearing of the eye bandage.

In a third preferred form of the present invention, the thickness of the peripheral portion is in the range of 0.3–0.7 mm. If the thickness of the peripheral portion is smaller than 0.3 mm, the peripheral portion does not exhibit rigidity sufficient for pressing the incised portion of the sclera with high stability. If the thickness of the peripheral portion exceeds 0.7 mm, the wearer may feel uncomfortable with the eye bandage worn on the eye.

In a fourth preferred form of the present invention, the eye bandage has a radial edge lift in the range of 0.5–2.0 mm. If the radial edge lift is smaller than 0.5 mm, the central portion of the eye bandage is spaced apart from or floats above the corresponding central region of the cornea surface when the eye bandage is worn on the eyeball. In this case, the central portion of the eye bandage is unfavorably corrugated, or air bubbles get into a spacing between the central portion of the eye bandage and the cornea surface, deteriorating the eyesight of the wearer. On the other hand, if the radial edge lift is larger than 2.0 mm, the edge of the peripheral portion is spaced apart from the sclera. In this case, the eye bandage is not capable of sufficiently pressing the incised portion of the sclera with pressing contact of the peripheral portion with the incised portion. As well known, the radial edge lift is a distance between a point on the back surface of the peripheral portion at its edge and a point which lies on an extension of the vertex sphere of the central portion, as measured along the radius of curvature of the central portion.

BRIEF DESCRIPTION OF THE DRAWINGS

The above and optional objects, features, advantages and technical significance of the present invention will be better understood by reading the following detailed description of a presently preferred embodiment of the invention, when considered in conjunction of the accompanying drawings, in which.

DETAILED DESCRIPTION OF THE PREFERRED EMBODIMENT

Figure 1:
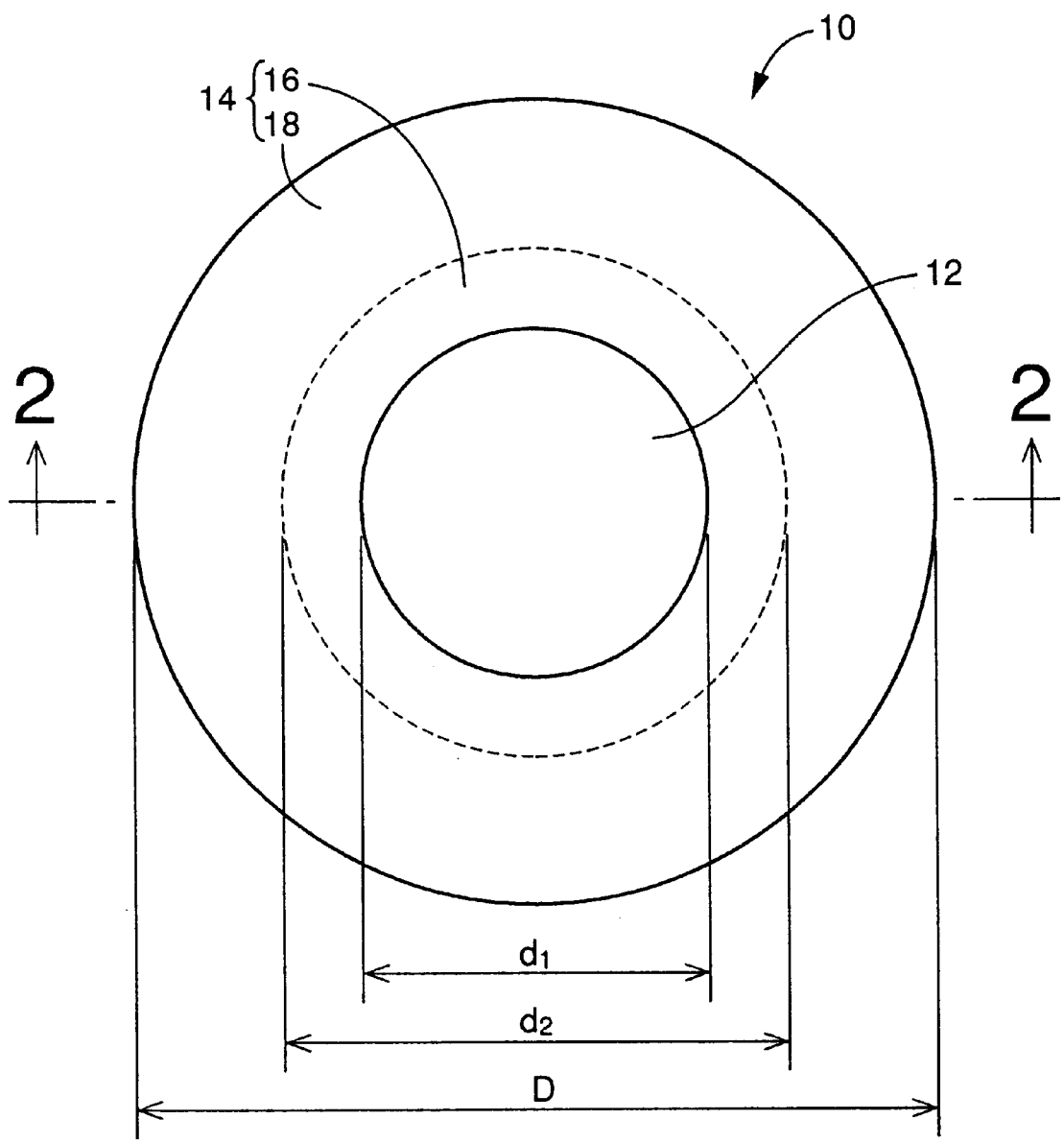
FIG. 1 is a plan view of an eye bandage constructed according to one embodiment of the present invention.
Figure 2:
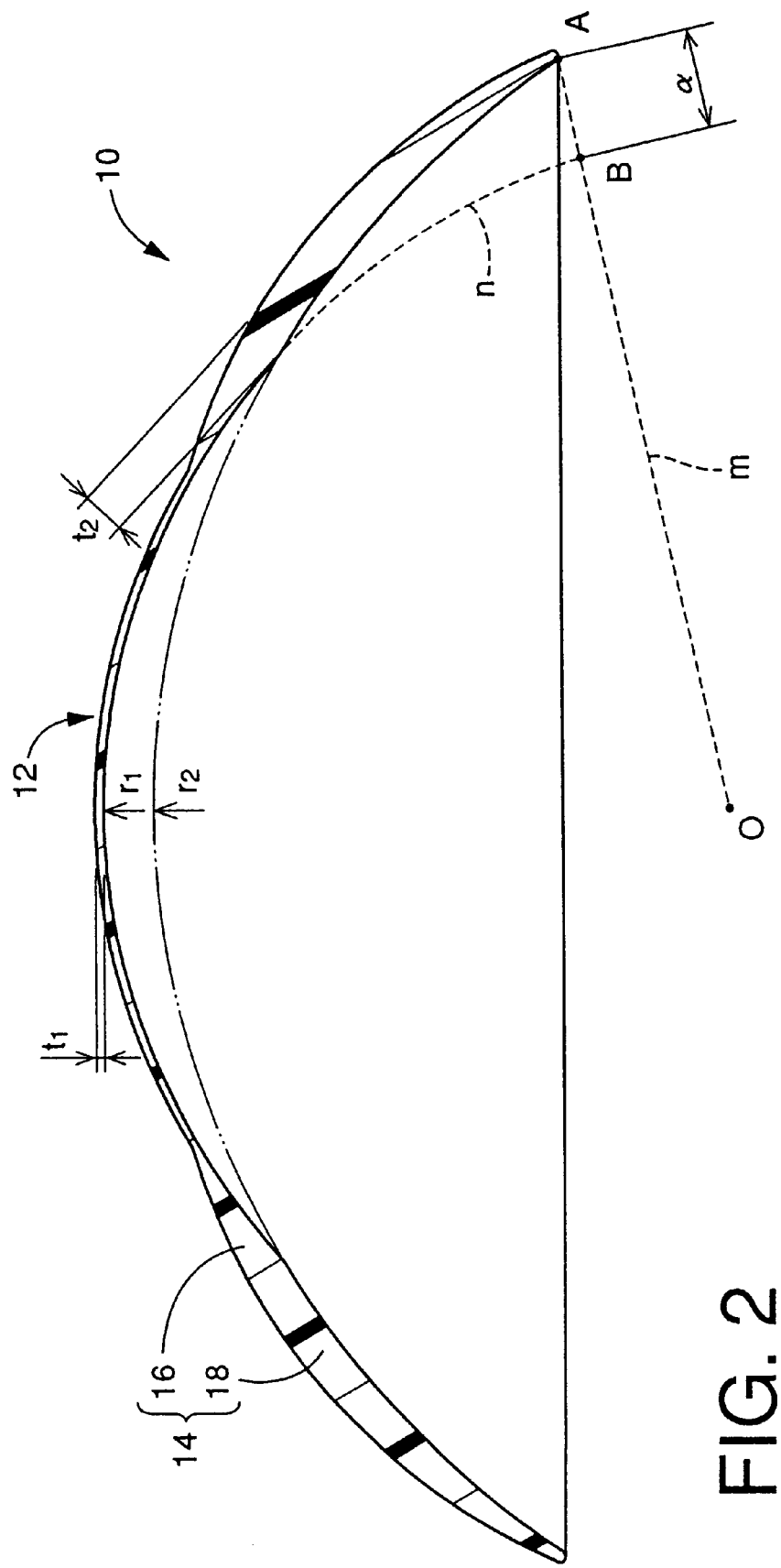
FIG. 2 is a cross sectional view, taken along line 2—2 of FIG. 1.

Referring to FIGS. 1 and 2, there is schematically shown an eye bandage constructed according to one embodiment of the present invention. This eye bandage 10 is worn on an eye of a patient after trabeculectomy which is a kind of an intraocular surgical operation to treat glaucoma. The eye bandage 10 of the present embodiment has a shape generally similar to that of a contact lens, and has a central portion 12 and a peripheral portion 14 whose front surfaces are shaped differently from each other.

Described more specifically, the eye bandage 10 is formed of polyhydroxyethyl methacrylate which is a known transparent soft material. The eye bandage 10 has a generally circular flat shape as seen in FIG. 1, having a diameter D of 18 mm. The diameter D of the eye bandage 10 is the outside diameter of the peripheral portion 14. This eye bandage 10 is easily worn on the eyeball after the eye is subjected to the trabeculectomy described above, so as to cover the entirety of the cornea and a portion of the sclera of the eye.

The central portion 12 of the eye bandage 10 corresponds to a central optical zone of the contact lens, and has a circular shape having a diameter d1 of 8 mm whose center is aligned with the center (optic center) of the eye bandage 10. When the eye bandage 10 is worn on the eyeball, the central portion 12 covers the corresponding central region of the cornea, such that the boundary or junction between the central portion 12 and the peripheral portion 14 is not located on or included in the visual field of the wearer. The back surface of the central portion 12 is an ellipsoidal, aspherical surface with a vertex radius of curvature r1 (indicated in FIG. 2) of 8 mm, and an eccentricity of 0.35. The thus formed back surface of the central portion 12 follows a profile of the front surface of the cornea of the eyeball on which the eye bandage 10 is placed. The central portion 12 has a thickness t1 (indicated in FIG. 2) of 0.08 mm, so as to assure easy fabrication of the eye bandage 10 as well as sufficient mechanical strength. Further, the central portion 12 having the above thickness is capable of permitting a sufficient amount of oxygen permeation therethrough, so that the oxygen can be effectively delivered to the cornea.

The peripheral portion 14 located radially outwardly of the central portion 12 corresponds to a peripheral zone of the contact lens, and consists of an annular cornea-contacting portion 16 which extends continuously from the outer periphery of the central portion 12, and an annular sclera-contacting portion 18 which extends continuously from the outer periphery of the cornea-contacting portion 16. The cornea-contacting portion 16 adjacent to the central portion 12 is concentric with the central portion 12, and has an outside diameter d2 (indicated in FIG. 1) of 11 mm. When the eye bandage 10 is worn on the eyeball, the cornea-contacting portion 16 covers an outer peripheral region of the cornea, which is not covered by the central portion 12. The sclera-contacting portion 18 adjacent to the cornea-contacting portion 16 covers a portion of the sclera located radially outwardly of the cornea, in particular, the incised portion formed in the sclera during the intraocular surgical operation of the eye.

The back surface of the cornea-contacting portion 16 is an ellipsoidal, aspherical surface which is continuously contiguous with the back surface of the central portion 12, so as to follow the profile of the front surface of the cornea, while the back surface of the sclera-contacting portion 18 is an ellipsoidal, aspherical surface with a vertex radius of curvature r2 (indicated in FIG. 2) of 10.382 mm, and an eccentricity of 0.35, so that the sclera-contacting portion 18 is held in close contact with the sclera while the eye bandage 10 is worn on the eyeball.

In the peripheral portion 14 consisting of the cornea-contacting portion 16 and the sclera-contacting portion 18, the thickness of the cornea-contacting portion 16 gradually increases in the radially outward direction from the central portion 12 toward the sclera-contacting portion 18, while the thickness of the sclera-contacting portion 18 gradually decreases in the radially outward direction from the cornea-contacting portion 16 toward the outer periphery of the peripheral portion 14. According to this arrangement, the peripheral portion 14 has the maximum thickness at the boundary or junction between the cornea-contacting portion 16 and the sclera-contacting portion 18. In the present eye bandage 10, the minimum thickness of the peripheral portion 14 is made larger than the thickness of the central portion 12. In the present embodiment, the maximum thickness t2 (indicated in FIG. 2) of the peripheral portion 14 at the boundary or junction between the cornea-contacting and sclera-contacting portions 16, 18 is 0.51 mm, so that the rigidity of the peripheral portion 14 is made considerably high without deteriorating the wearing comfort of the eye bandage 10 as felt by the wearer.

The eye bandage 10 according to the present embodiment has a radial edge lift (REL) of 1.05 mm. As indicated in FIG. 2, the radial edge lift is a distance α on a line segment m which connects a point A and a point O, wherein the point A lies on the back surface of the peripheral portion 14 at its edge, and the point O is the center of curvature of the back surface of the central portion 12. More specifically described, the radial edge lift is the distance α between the above-indicated point A and a point B which is an intersection of the line segment m and an extension of a vertex sphere of the central portion 12. When the thus constructed eye bandage 10 is placed on the eyeball, the central portion 12 and the edge of the peripheral portion 14 are held in close contact with the cornea and the sclera, respectively, without any clearance between the back surface of the eye bandage 10 and the front surfaces of the cornea and the sclera.

In the eye bandage 10 constructed according to the present embodiment, the thickness of the peripheral portion 14 is made larger than that of the central portion 12, so that the peripheral portion 14 exhibits a sufficiently high degree of rigidity. The thus formed eye bandage 10 is placed on the eyeball which has been subjected to the trabeculectomy, such that the thin-walled central portion 12 is held in close contact with the cornea, and such that the thick-walled, rigid peripheral portion 14 is held in pressing contact with the sclera at its sclera-contacting portion 18 while covering the entirety of the incised portion of the sclera formed in the surgical operation. According to this arrangement, even when the filtration blebs are formed in the incised portion of the sclera due to accumulation of the aqueous humor, the sclera-contacting portion 18 covering the incised portion is capable of pressing the filtration blebs owing to its rigidity without suffering from otherwise possible flexural or bending deformation. Furthermore, the thick-walled, rigid peripheral portion 14 can be tightly pressed against the sclera by the eye lid when the eye bandage 10 is placed of the eyeball.

The present eye bandage 10 is worn on the eyeball after the trabeculectomy to treat the glaucoma, so as to sufficiently press the incised portion of the sclera and the filtration blebs formed in the incised portion in the surgical operation, to thereby effectively prevent the excessive drainage or run-off of the aqueous humor from the filtration blebs. Accordingly, the present eye bandage 10 allows early recovery and effective protection of the eye after the intraocular surgical operation.

The eye bandage 10 is formed of polyhydroxyethyl methacrylate which is a well-known and widely-used soft material, permitting easy manufacture of the eye bandage 10 and giving the wearer an excellent wearing comfort like the conventional soft contact lens formed of such a soft material.

The central portion 12 of the present eye bandage 10 which is to contact the cornea has a considerably small thickness, to thereby permit permeation of a sufficient amount of oxygen therethrough. Therefore, the cornea does not suffer from any damage which would be caused by shortage of oxygen during continuous wearing of the eye bandage 10 on the eye. Furthermore, the eye bandage 10 having the central portion 12 with such a small thickness can be easily fabricated and has sufficient mechanical strength.

In the present eye bandage 10, the outside diameter of the peripheral portion 14 (i.e., the diameter of the eye bandage 10) is 18 mm, whereby the eye bandage is easily placed on the eyeball. Further, the thickness of the peripheral portion is about 0.51 mm, so that the wearer does not feel uncomfortable when the eye bandage 10 is placed on the eyeball. Thus, the present eye bandage 10 assures the wearer of comfortable wearing.

In the present eye bandage 10, the amount of the radial edge lift is determined such that the central portion 12 and the edge of the peripheral portion 14 do not float away from the front surfaces of the cornea and the sclera, respectively, to thereby avoid formation of any spacing between the back surface of the eye bandage 10 and the front surfaces of the cornea and the sclera. This arrangement is free from the problems that the central portion 12 is corrugated and that the air bubbles get into the spacing between the back surface of the eye bandage 10 and the front surfaces of the cornea and the sclera. Accordingly, the present eye bandage 10 does not cause any trouble to the vision of the wearer while assuring the application of a sufficiently large force by the thick-walled peripheral portion 14 for pressing the incised portion of the sclera and the filtration blebs formed in the incised portion.

In the illustrated embodiment, the eye bandage 10 is dimensioned such that the diameter of the central portion 12 is 8 mm, while the outside diameter of the cornea-contacting portion 16 is 11 mm and the outside diameter of the sclera-contacting portion 18 of the peripheral portion 14 is 18 mm. However, the dimensions of the eye bandage 10 are not limited to those of the illustrated embodiment. For instance, the outside diameter of the sclera-contacting portion 18 of the peripheral portion 14 (i.e., the diameter of the eye bandage 10) is preferably in the range of 16–22 mm, so that the eye bandage 10 can be easily placed on the eyeball and effectively cover the entire incised portion of the sclera. The diameter of the central portion 12 and the outside diameter of the cornea-contacting portion 16 of the peripheral portion 14 are suitably determined depending upon the size of the corneas of the individual patients.

The central portion 12 of the eye bandage 10 in the illustrated embodiment has a thickness of 0.08 mm. It is preferable that the thickness of the central portion 12 be in the range of 0.03–0.15 mm for permitting permeation of a sufficient amount of oxygen through the central portion, without deteriorating the ease of manufacture of the eye bandage 10 and lowering the mechanical strength of the eye bandage 10.

The peripheral portion 14 of the eye bandage 10 in the illustrated embodiment has the maximum thickness of 0.51 mm. It is preferable that the thickness of the peripheral portion 14 be in the range of 0.3–0.7 mm, to thereby assure a sufficient force to press the incised portion of the sclera and the filtration blebs formed in the incised portion while assuring the wearer of comfortable wearing of the bandage.

The eye bandage 10 of the illustrated embodiment has the radial edge lift of 1.05 mm. The radial edge lift is preferably in the range of 0.5–2.0 mm so as to prevent the central portion 12 and the edge of the peripheral portion 14 of the eye bandage 10 from floating away from the cornea and the sclera, respectively, while the eye bandage 10 is placed on the eyeball.

Although the eye bandage 10 in the illustrated embodiment is formed of polyhydroxyethyl methacrylate which is a known transparent soft material, the eye bandage 10 may be formed of other transparent soft materials which are used for producing conventional eye bandages and soft contact lenses for rectifying the eyesight. Examples of such soft materials are polymers which contain as a major component: alkyl methacrylates such as propyl methacrylate, butyl methacrylate, pentyl methacrylate and hexyl methacrylate; alkyl acrylates such as propyl acrylate, butyl acrylate, pentyl acrylate and hexyl acrylate; hydroxyl group-containing alkyl methacrylates such as dihydroxypropyl methacrylate; hydroxy group-containing alkyl acrylates such as hydroxyethyl acrylate and dihydroxypropyl acrylate; N-vinylactams such as N-vinylpyrrolidone; or acrylamide such as dimethyl acrylamide. The eye bandage 10 may be formed of a silicone rubber or an acrylic rubber, for instance.

In the illustrated embodiment, the back surface of the central portion 12 is the ellipsoidal, aspherical surface having the radius of curvature r1 of 8 mm and the eccentricity of 0.35, while the back surface of the peripheral portion 14 is the ellipsoidal, aspherical surface having the radius of curvature r2 of 10.382 mm and the eccentricity of 0.35. The configurations of the back surfaces of the central and the peripheral portions 12, 14 are not limited to those of the illustrated embodiment. The back surfaces of the central and the peripheral portions 12, 14 may be other ellipsoidal, aspherical surfaces or spherical surfaces whose values of the radius of curvature and eccentricity are different from those specified above, provided that the back surface of the central portion 12 is held in contact with the cornea, and that the back surface of the peripheral portion 14 is held in pressing contact with the sclera.

While the illustrated embodiment is directed to the eye bandage which is worn on the eyeball after the trabeculectomy to treat the glaucoma, the principle of the present invention is equally applicable to other kinds of eye bandages adapted to be worn on eyes subjected to intraocular surgical operations other than the trabeculectomy.

While the present invention has been described in its presently preferred embodiment, it is to be understood that the invention is not limited to the details of the illustrated embodiment, but may be embodied with other changes, modifications and improvements which may occur to those skilled in the art, without departing from the spirit and scope of the invention defined in the attached claims.

What is claimed is:

1. An eye bandage formed of a soft material and having a shape similar to a contact lens, said eye bandage being worn on an eye after an intraocular surgical operation of the eye, such that said eye bandage is held in contact with a cornea and a sclera of the eye so as to cover an incised portion of the sclera, said eye bandage comprising:

a central portion adapted to contact the cornea and which has a back surface having a profile following that of a front surface of the cornea; and a peripheral portion located radially outwardly of said central portion and having a thickness larger than that of said central portion and a diameter which is large enough to cover the incised portion of the sclera, said peripheral portion including at least a sclera-contacting portion adapted to contact the sclera, said sclera-contacting portion having a back surface having a profile following a front surface of the sclera, so that said sclera-contacting portion is held in close contact with the sclera of the eye during use.

2. An eye bandage according to claim 1, wherein an outside diameter of said peripheral portion is in a range of 16–22 mm.

3. An eye bandage according to claim 1, wherein said central portion has a thickness in a range of 0.03–0.15 mm.

4. An eye bandage according to claim 1, wherein said peripheral portion has a thickness in a range of 0.3–0.7 mm.

5. An eye bandage according to claim 1, having a radial edge lift in a range of 0.5–2.0 mm.

6. An eye bandage according to claim 1, wherein said central portion is to contact a corresponding central region of the cornea, said peripheral portion further including a cornea-contacting portion which is adjacent to said central portion and adapted to contact an outer peripheral region of the cornea.

7. An eye bandage according to claim 1, wherein said soft material comprises polymers which contain as a major component at least one monomer selected from the group consisting of alkyl methacrylates, alkyl acrylates, hydroxyl group-containing alkyl methacrylates, hydroxy group-containing alkyl acrylates, N-vinylactams, and acrylamide.

8. An eye bandage according to claim 1, wherein said soft material comprises a silicone rubber.

9. An eye bandage according to claim 1, wherein said soft material comprises polyhydroxyethyl methacrylate.

10. An eye bandage according to claim 1, wherein said soft material comprises an acrylic rubber.

* * * * *